US00PP13963P39

(12) United States Plant Patent
Stribling

(10) Patent No.: US PP13,963 P3
(45) Date of Patent: Jul. 8, 2003

(54) FICUS PLANT NAMED 'MINI AMSTEL'

(75) Inventor: Sally Stribling, Homestead, FL (US)

(73) Assignee: Miami Agra-Starts, Inc., Homestead, FL (US)

( * ) Notice: Subject to any disclaimer, the term of this patent is extended or adjusted under 35 U.S.C. 154(b) by 0 days.

(21) Appl. No.: 09/880,880

(22) Filed: Jun. 15, 2001

(65) Prior Publication Data

US 2002/0194656 P1 Dec. 19, 2002

(51) Int. Cl.[7] ..... A01H 5/00
(52) U.S. Cl. ..... Plt./211
(58) Field of Search ..... Plt./211

(56) References Cited

U.S. PATENT DOCUMENTS

PP9,856 P * 4/1997 Van Geest ..... Plt./88.9

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Ficus plant named 'Mini Amstel', as described and illustrated, and particulary characterized by the combined features of 40–45 mm wide leaves with elongated, lanceolate shape; medium green leaves closest to RHS 137 A; and irregular internodes with zig-zag pattern.

4 Drawing Sheets

Latin name of the genus and species of the plant claimed: *Ficus benjamina.*

Variety denomination: Mini Amstel.

BACKGROUND OF THE INVENTION

The present invention relates to a new and distinct cultivar of *Ficus benjamina.* The varietal denomination of the new cultivar is 'Mini Amstel'.

The new variety was discovered as a naturally occurring sport mutation of an unnamed variety of *Ficus benjamina,* amongst a controlled planting of *Ficus benjamina* plants. The new variety was selected by the inventor, Sally Stribling, at a controlled outdoor planting in July, 1999. The new variety was first asexually propagated by vegetative cuttings in October, 1999, in Homestead, Fla. Asexual reproduction by vegetative cuttings through succeeding generations has established that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Mini Amstel' which in combination distinguish this Ficus as a new and distinct cultivar:

1. 40–45 mm wide leaves with elongated, lanceolate shape;
2. medium green leaves closest to RHS 137 A; and
3. irregular internodes with zig-zag pattern.

'Mini Amstel' varies from the parent plant in leaf size and shape. The leaves of 'Mini Amstel' are wider, 40–45 mm, and longer, 112 mm, have an elongated lanceolate shape, no undulation to the leaf margins. The leaves of the unnamed parent plant are narrower, approximately 30–36 mm in width, shorter, approximately 82 mm in length, ovate in shape, and have undulating leaf margins. The banana shaped leaf of 'Mini Amstel' is approximately half the length of the leaf of the Ficus variety named 'Amstel King'. Ficus 'Amstel King' and 'Mini Amstel' are not related as 'Amstel King' is a Macllelandii type Ficus and 'Mini Amstel' is a *Ficus benjamina.*

BRIEF DESCRIPTION OF THE DRAWINGS

The accompanying photographic drawings illustrate the overall appearance of the new Ficus cultivar, showing colors as true as is reasonably possible with color reproductions of this type . The first photographic drawing shows the typical characteristics of a Ficus 'Mini Amstel' plant in its entirety.

The second photographic drawing shows the leaves of the unnamed parent plant on the left, the leaves of 'Mini Amstel' in the center, and the leaves of 'Midnight' on the right.

The third photographic drawing is a close-up of the leaves of 'Mini Amstel' showing the elongated lanceolate shape and the leaf and mid-vein colors.

The fourth photographic drawing is a close-up of the leaves of the comparison cultivar, 'Midnight', showing the ovate shape and leaf and mid-vein colors.

DETAILED DESCRIPTION OF THE NEW VARIETY

'Mini Amstel' has not been observed under all possible environmental conditions. The phenotypic expression may vary with variations in environment such as temperature, light intensity, day length and cultural conditions, without a change in the genotype of the plant.

The following observations and descriptions are of a 6 month old plant grown in Homestead, Fla. in an unheated, open air shade house from October, 2000 until April, 2001. The shade cloth on the structure has a 73% shade factor. In this description, color references are to The Royal Horticultural Society Colour Chart (R.H.S.). The color references are approximate as color depends to a degree on horticultural practices such as light level and fertilization rates.

Plant:

*Form.*—An Upright woody multiple irregular branching Ficus with slightly zig-zagging internodes and elongated lanceolate shaped leaves.

*Growth.*—Upright multiple branching.

*Height.*—Height attained as of April, 2001, 1.5 meters. This height has been maintained by pruning in controlled plantings in a shade house in Homestead, Fla.

Foliage:

*Size.*—7–11 cm long; 40–45 mm wide.

*Quantity.*—Numerous multiple.

*Color.*—Mature leaves: Upperside medium green closest to RHS 137 A; underside green RHS 137 D. Immature leaves: Upperside RHS 143C; underside RHS 144 C.

*Shape.*—Lanceolate elongate with Acuminate leaf tip.

*Texture.*—Smooth and glabrous.

*Veination.*—Single mid-rib vein, RHS 146 D under side of leaf from petiole to leaf tip typical of *benjamina* type Ficus.

*Edge.*—Smooth.

*Serration.*—None.

*Stipules.*—None.

*Auricle.*—None.

*Petiole.*—Irregular between 15–35 mm in length; RHS 137 C in color.

Disease/insect resistance: No particular claim is made in reference to disease resistance. It has been observed to be susceptible to Thrips and Spider mites just as the parent plant.

*Rachis.*—Not apparent.

Wood:

*New shoots.*—Medium greyed-green closest to RHS 197B.

*Old wood.*—Greyed-green between 197C and 197D.

Internode spacing: Irregular, between 29–35 mm.

Preferred growing conditions: 25–35 degrees centigrade under 5,000 foot candles.

Reproductive organs: None observed.

We claim:

1. A new and distinct variety of Ficus plant designated 'Mini Amstel', substantially as illustrated and described.

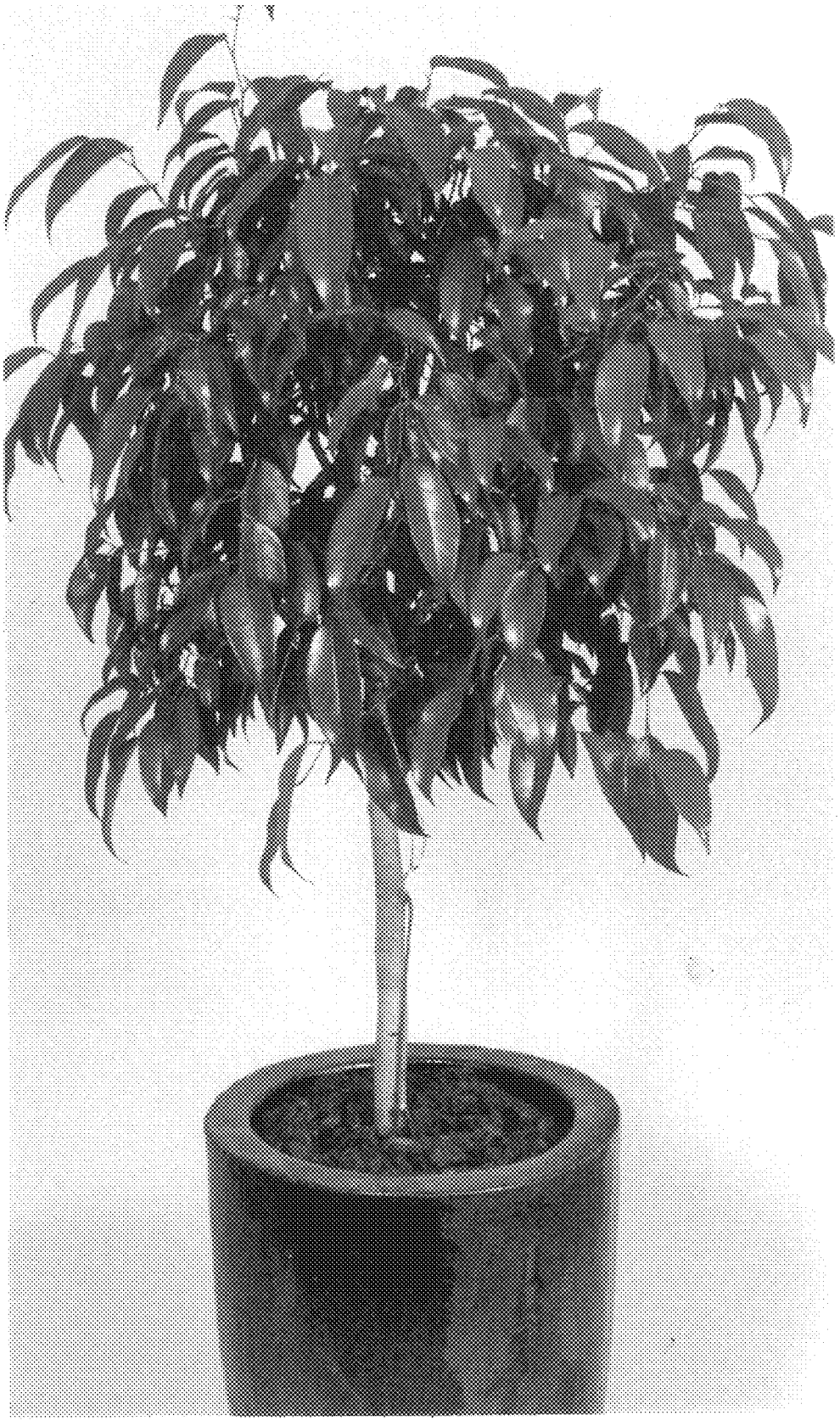

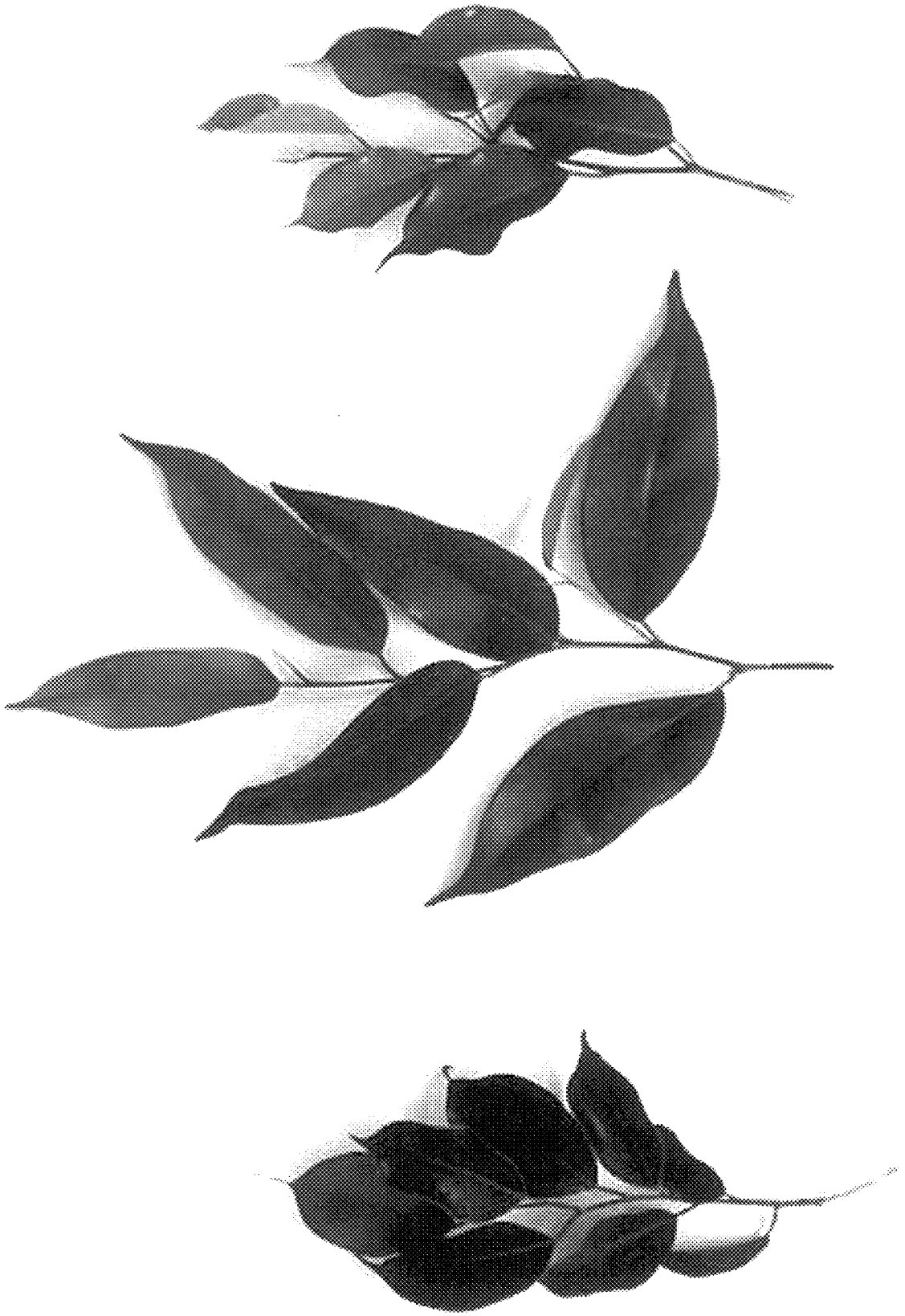

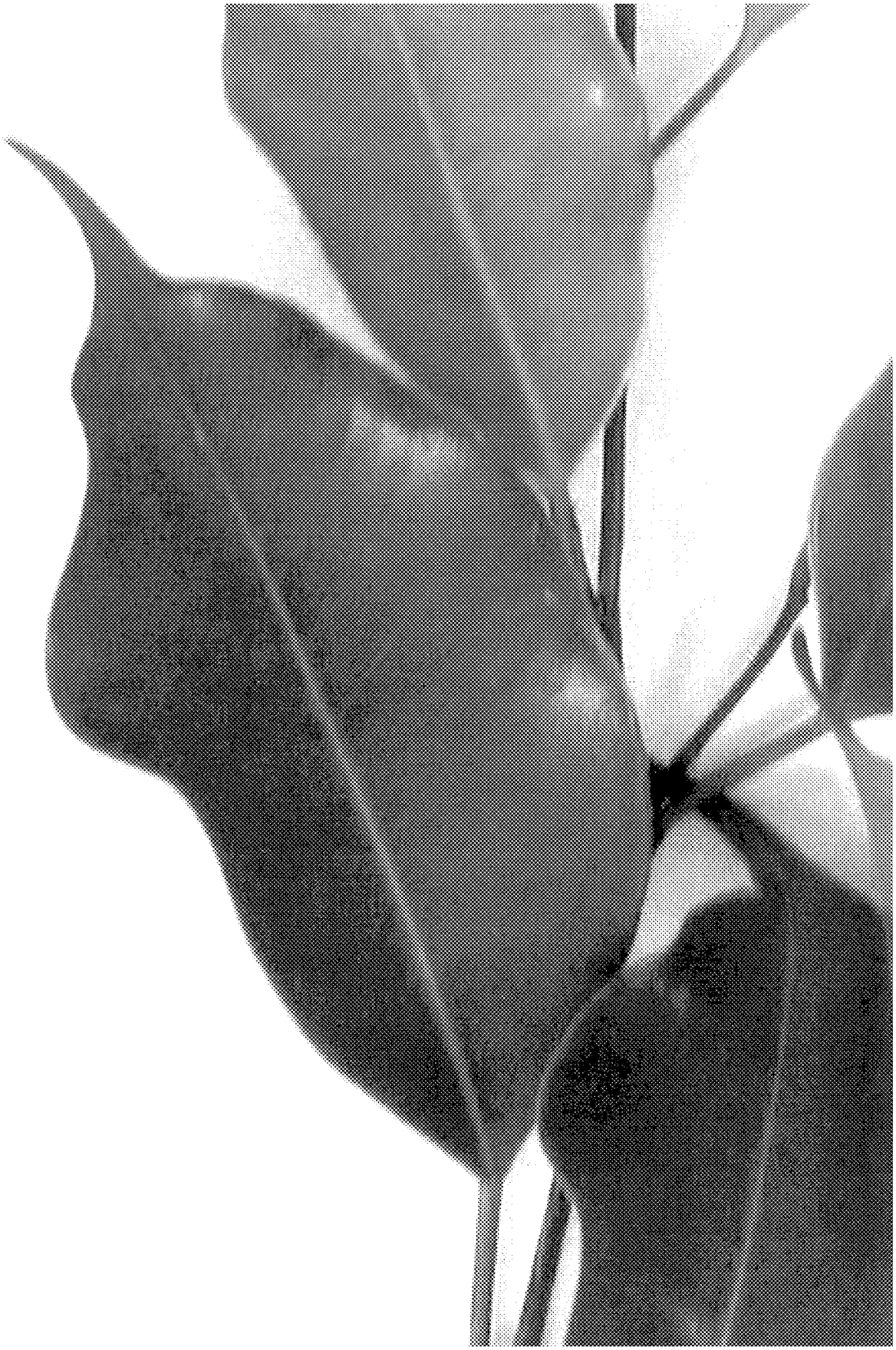

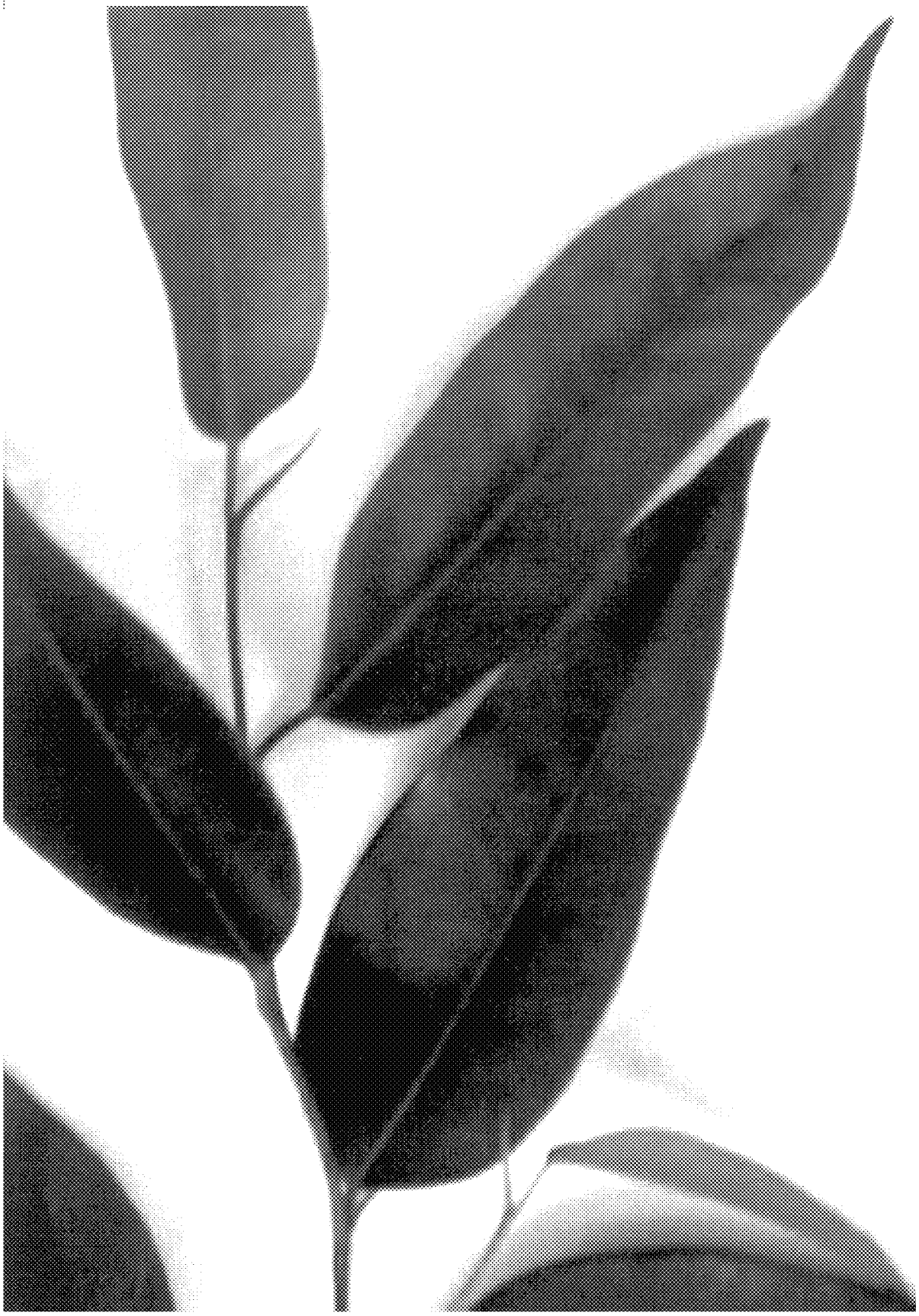

* * * * *